United States Patent [19]

Wu

[11] Patent Number: 5,489,564
[45] Date of Patent: Feb. 6, 1996

[54] ALKANE DISPROPORTIONATION

[75] Inventor: An-hsiang Wu, Bartlesville, Okla.

[73] Assignee: Phillips Petroleum Company, Bartlesville, Okla.

[21] Appl. No.: 299,761

[22] Filed: Sep. 7, 1994

[51] Int. Cl.$^6$ ................................................ B01J 21/02
[52] U.S. Cl. .............................. 502/203; 502/202
[58] Field of Search ...................... 502/202, 203

[56] References Cited

U.S. PATENT DOCUMENTS

| | | |
|---|---|---|
| 3,766,286 | 10/1973 | Olah . |
| 3,878,261 | 4/1975 | Gardner . |
| 4,547,474 | 10/1985 | Olah ........................................ 502/168 |
| 4,697,007 | 9/1987 | Spitz et al. ............................. 502/168 |
| 4,814,544 | 3/1989 | Olah ........................................ 585/747 |
| 4,847,223 | 7/1989 | Le Van Mao et al. .................. 502/62 |
| 5,110,778 | 5/1992 | Olah ........................................ 502/202 |
| 5,233,119 | 8/1993 | Kallenbach et al. ................... 585/721 |
| 5,245,103 | 9/1993 | Wu .......................................... 585/743 |
| 5,288,685 | 2/1994 | Kallenbach et al. ................... 502/168 |
| 5,292,986 | 3/1994 | Abbott .................................... 502/150 |

OTHER PUBLICATIONS

"Superacid–Catalyzed Isomerization of endo–to exo–Trimethyleneorborane (Tetrahydrodicyclopentadiene) and to Adamantane," Olah et al., J. Org. Chem. 51, pp. 5410–5413, 1986 no month available.

"Chemistry in Superacids. 6. Perfluoralkanesulfonic Acid–Boron Perfluoroalkanesulfonates: New Superacid Systems for Generation of Carbocations and Catalysts for Electrophilic Transformations of Hydrocarbons," Olah et al., J. Org. Chem. 49, pp. 4591–4594, 1984 no month available.

*Primary Examiner*—E. Rollins Cross
*Assistant Examiner*—E. D. Irzinski
*Attorney, Agent, or Firm*—M. H. Michel

[57] ABSTRACT

A catalyst useful in the disproportionation of alkanes is provided comprising an acid component having the formula $HB(OSO_2CF_3)_4$ and a support. A method for the disproportionation of $C_4$–$C_{16}$ alkanes employing the catalyst is also provided.

9 Claims, No Drawings

ALKANE DISPROPORTIONATION

BACKGROUND OF THE INVENTION

The present invention relates to alkane disproportionation.

By disproportionation is meant the process by which a portion of at least one feed alkane is converted to alkane product containing at least one product alkane having higher molecular weight and at least one product alkane having lower molecular weight.

Low-boiling alkanes (such as butanes and pentanes) are components of gasoline fuels. Recent governmental regulations mandate that the vapor pressure of gasoline fuels be lowered. Consequently, the content of these low-boiling alkanes in gasoline will have to be reduced. It would therefore be desirable to develop a process for converting a portion of these low-boiling alkanes to higher-boiling alkanes which are environmentally more acceptable as motor fuel components. It would also be desirable to provide a catalyst which is easily separated from the alkane product and capable of reuse for long periods of time.

SUMMARY OF THE INVENTION

It is an object of this invention to provide a process to partially disproportionate alkanes to higher-boiling and lower boiling alkanes.

It is another object of this invention to provide a catalyst which is easily separated from the alkane product.

It is another object of this invention to provide a catalyst capable of extended use in multiple cycles.

It is another object of this invention to provide a catalyst providing improved conversion to higher-boiling alkanes.

In accordance with the present invention a catalyst useful in the disproportionation of alkanes is provided comprising and acid component having the formula $HB(OSO_2CF_3)_4$ and a support. In accordance with another aspect of the invention, a method for the disproportionation of alkanes is also provided.

DETAILED DESCRIPTION OF THE INVENTION

The present invention concerns disproportionation of alkanes employing a supported catalyst comprising an acid component represented by the formula $HB(OSO_2CF_3)_4$ and a support.

The acid component can be prepared by reacting a boron compound and trifluoromethanesulfonic acid (also called triflic acid) represented by the formula $CF3OSO2H$, wherein the boron compound is selected from the group consisting of boron trihalide represented by the formula $BX_3$, wherein X is a halide, preferably bromide, and boron phosphate. Generally the triflic acid will be present in an amount in the range of from about 1 mole to about 10 moles per mole-of boron compound, preferably from about 1 mole to about 8 moles, and more preferably from 2 moles to 6 moles per mole of boron compound. The conditions for reacting the boron compound and triflic acid can vary broadly. Generally the reaction will be conducted at a temperature in the range of from about 0° C. to about 100° C., preferably from 10° C. to 90° C.

Typical supports useful in the invention include alumina, silica, silica-alumina, aluminosilicates (clays, zeolites), titania, zirconia, hafnia, carbon, aluminum phosphate, aluminum oxide/phosphate, aluminum borate, aluminum oxide/borate, aluminum sulfate, aluminum oxide/sulfate, boron oxide, boron phosphate, boron oxide/phosphate, boron sulfate, boron oxide/sulfate, sulfonated ion-exchange resins (such as sulfonated styrene polymers), and mixtures thereof. Silica-containing supports are preferred. Excellent results have been obtained with silica and it is especially preferred. Many suitable supports are commercially available. Generally, the surface area of such supports is in the range of about 200 to about 400 m$^2$/g (determined by the method of Brunauer, Emmett and Teller employing $N_2$). Preferably, the supports have a particle size in the range of from about 0.4 mm to about 3.2 mm.

Generally the acid component is present in an amount in the range of from about 0.1 gram to about 10 grams per gram of support, preferably from about 0.2 gram to about 8 grams, and more preferably 0.5 gram to 5 grams per gram of support. The conditions for contacting the acid component and the support can vary broadly and are those sufficient to impregnate the support with the acid component. Generally the temperature will be in a range of from about 0 ° C. to about 100° C.

Suitable feed alkanes includes alkanes having 4 to 16 carbon atoms per molecule, preferably 4 to 12 carbon atoms per molecule, and more preferably 4 to 8 carbon atoms per molecule. These alkanes can be straight-chain alkanes (normal alkanes) or branched alkanes. Typical examples of suitable alkanes include n-butane, isobutane, n-pentane, isopentane, n-hexane, 2-methylpentane, 3-methylpentane, 2,2-dimethylbutane, n-heptane, methyl-substituted hexanes, dimethyl-substituted pentanes, n-octane, methyl-substituted heptanes, dimethyl-substituted hexanes, n-nonane, methyl-substituted octanes, dimethyl-substituted heptanes, trimethyl-substituted hexanes, n-decane, methyl-substituted nonanes, dimethyl-substituted octanes, trimethyl-substituted heptanes, tetramethyl-substituted hexanes, normal and branched undecanes, normal and branched dodecanes, and mixtures thereof.

The process of this invention for converting at least one feed alkane to product alkanes can be carried out under any suitable reaction conditions from about 0° C. to about 100° C., preferably about 10° C. to about 80° C., more preferably from 20° C. to 50° C., generally at 1 to 5 atmospheres pressure. The at least one feed alkane can be contacted with the catalyst composition in any suitable manner, such as in a slurry-type operation in which the catalyst components are dispersed in the alkane feed, or in a moving catalyst bed operation where alkane feed and catalyst components move in the same direction, or in a fixed catalyst bed operation in which the alkane feed flows upward or downward through a catalyst layer or layers. The time of contact between the alkane feed and the catalyst generally is in the range of from about 5 minutes to about 30 hours, preferably from about 5 minutes to about 24 hours, and more preferably from 30 minutes to 20 hours.

The process of this invention produces multiple alkanes in the alkane product. Thus, it may be desirable to separate the various alkanes from one another. This separation and recovery of the various products can be carried out in any suitable manner known in the art, generally by fractional distillation. As indicated above, higher boiling fractions can be recovered and used in gasoline fuels. Isobutane can be further processed, as is known in the art, to produce higher alkylate products.

The following examples will serve to show the present invention in detail by way of illustration and not by way of limitation.

EXAMPLES

EXAMPLE 1

Example 1 demonstrates the effectiveness of a catalyst comprising the acid component $HB(OSO_2CF_3)_4$ and a support compared to catalysts of unsupported triflic acid or unsupported acid component.

The disproportionation process in the following samples was conducted by charging the indicated catalysts into a 300 cc 316SS autoclave which had been purged with He for 15 minutes. The catalysts were prepared by combining the reagents indicated with 3.00 g triflic acid prior to charging to the reactor. Control Runs 101, 104, 107, and 110 employed triflic acid as catalyst. Runs 102, 105, 108, and 111 employed the acid component as catalyst. The acid component was prepared by adding 3.00 g triflic acid to a reaction flask containing 1.25 g $BBr_3$ under argon. Runs 103, 106, 109, and 112 employed the inventive supported catalyst. The supported catalyst was prepared by adding 5 ml Freon 113 to the acid component prepared as described above and impregnating 5.00 g Davison G-57 12–20 mesh silica with the acid component. In each run 50.00 g n-pentane was added to the autoclave through a G-57 silica column. The pressure in the autoclave was maintained with He as indicated. The reaction mixture was stirred at 1400 rpm for 16 hours. The final alkane product was collected in a sample vessel prechilled at −78° C. and analyzed by means of a gas chromatograph. The results are tabulated in Table 1.

In Table 1:
$BBr_3$ is the grams boron tribromide employed in the catalyst,
$SiO_2$ is the grams silica support employed in the catalyst,
$CO_2$ is the partial pressure $CO_2$ in psig,
Press. is the total pressure in the reactor in psig,
n-C5 is the weight percent n-pentane in the alkane product,
i-C4 is the weight percent isobutane in the alkane product,
i-C5 is the weight percent isopentane in the alkane product, and
C6+ is the weight percent n-hexane plus heavier alkanes in the alkane product.

TABLE 1

| Run | $BBr_3$ g | $SiO_2$ g | $CO_2$ psig | Press. psig | n-C5 wt-% | i-C4 wt-% | i-C5 wt-% | C6+ wt-% |
| --- | --- | --- | --- | --- | --- | --- | --- | --- |
| 101 | 0 | 0 | 0 | 0 | 99.95 | 0 | 0.05 | 0 |
| 102 | 1.25 | 0 | 0 | 0 | 32.9 | 13.1 | 33.6 | 19.9 |
| 103 | 1.25 | 5.00 | 0 | 0 | 16.8 | 16.6 | 41.0 | 24.9 |
| 104 | 0 | 0 | 0 | 500 | 99.95 | 0 | 0.05 | 0 |
| 105 | 1.25 | 0 | 0 | 500 | 31.8 | 12.7 | 33.5 | 21.4 |
| 106 | 1.25 | 5.00 | 0 | 500 | 15.6 | 15.8 | 41.5 | 26.5 |
| 107 | 0 | 0 | 0 | 1050 | 99.95 | 0 | 0.05 | 0 |
| 108 | 1.25 | 0 | 0 | 1050 | 32.0 | 12.4 | 33.5 | 21.3 |
| 109 | 1.25 | 5.00 | 0 | 1050 | 16.2 | 15.7 | 40.9 | 26.6 |
| 110 | 0 | 0 | 200 | 1050 | 99.95 | 0 | 0.05 | 0 |
| 111 | 1.25 | 0 | 200 | 1050 | 31.5 | 13.0 | 31.8 | 23.3 |
| 112 | 1.25 | 5.00 | 200 | 1050 | 16.1 | 15.0 | 41.4 | 26.8 |

The results in Table 1 demonstrate the effectiveness of employing a catalyst comprising an acid component and a silica support as evidenced by the increased n-C5 conversion, i.e. decreased concentration of n-C5 in the alkane product, and increased heavy fraction, C6+ concentration, compared to employing triflic acid or unsupported acid component as catalyst.

EXAMPLE 2

Example 2 demonstrates the reusability of the inventive catalyst.

The disproportionation process was conducted employing a catalyst prepared as follows.

The catalyst was prepared by impregnating silica with the acid component $HB(OSO_2CF_3)_4$. The acid component was prepared by adding 3.00 g triflic to a reaction flask containing 1.25 g $BBr_3$ under argon. After 15 minutes, 5 mL Freon 113 was added. Davison G-57 12–20 mesh silica was dried and 5.00 g of the silica was impregnated with the acid component to produce the supported acid catalyst. In each cycle, 50.00 g n-pentane was added to the autoclave through a G-57 silica column. The pressure in the autoclave was maintained with He at 500 psig. The reaction mixture was stirred at 1400 rpm for 16 hours. The final alkane product was collected in a sample vessel prechilled at −78° C. and analyzed by means of a gas chromatograph. Six cycles were completed employing the same catalyst. The results are tabulated in Table 2.

In Table 2:
Cycle # represents number of times the catalyst was employed,
Conv. is the percent conversion of n-pentane,
i-C4 is the weight percent isobutane in the alkane product,
i-C5 is the weight percent isopentane in the alkane product, and
C6+ is the weight percent n-hexane plus heavier alkanes in the alkane product.

TABLE 2

| Cycle # | Conv. % | i-C4 wt-% | i-C5 wt-% | C6+ wt-% |
| --- | --- | --- | --- | --- |
| 1 | 83.6 | 15.3 | 40.9 | 26.8 |
| 2 | 84.4 | 15.9 | 40.0 | 27.9 |
| 3 | 83.7 | 16.0 | 39.8 | 27.2 |
| 4 | 83.1 | 16.0 | 39.6 | 26.8 |
| 5 | 82.9 | 16.0 | 39.0 | 27.2 |
| 6 | 81.2 | 15.2 | 40.0 | 26.3 |

The results in Table 2 demonstrate the long term effectiveness of a catalyst comprising an acid component and silica, as indicated by the consistently high % conversion of n-C5 and relatively high selectivity to C6+ heavy alkanes even after 6 cycles.

That which is claimed is:

1. A catalyst useful for disproportionation of alkanes comprising an acid component represented by the formula $HB(OSO_2CF_3)_4$ and a support selected from the group consisting of alumina, silica, silica-alumina, aluminosilicates, titania, zirconia, hafnia, carbon, aluminum phosphate, aluminum oxide/phosphate, aluminum borate, aluminum oxide/borate, aluminum sulfate, aluminum oxide/sulfate, boron oxide, boron phosphate, boron oxide/phosphate, boron sulfate, boron oxide/sulfate, sulfonated ion-exchange resins, and mixtures thereof.

2. A catalyst according to claim 1 wherein said support is silica, silica-alumina, or aluminosilicates.

3. A catalyst according to claim 2 wherein said support is silica.

4. A catalyst according to claim 1 wherein said acid component is present in an amount in the range of from about 0.1 gram to about 10 grams per gram of support.

5. A catalyst according to claim 4 wherein said acid component is present in an amount in the range of from about 0.2 gram to about 8 grams per gram of support.

6. A catalyst according to claim 5 wherein said acid component is present in an amount in the range of from 0.5 gram to 5 grams per gram of support.

7. A catalyst according to claim 1 wherein said acid component is prepared by reacting a boron compound and trifluoromethanesulfonic acid, wherein said boron compound is a boron trihalide or boron phosphate.

8. A catalyst according to claim 7 wherein said boron compound is boron tribromide.

9. A catalyst useful for disproportionation of alkanes consisting essentially of an acid component represented by the formula $HB(OSO_2CF_3)_4$ and a support.

* * * * *